US008571698B2

(12) United States Patent
Chen et al.

(10) Patent No.: US 8,571,698 B2
(45) Date of Patent: Oct. 29, 2013

(54) SIMPLE TECHNIQUES FOR THREE-DIMENSIONAL MODELING

(75) Inventors: Jian Chen, Cambridge, MA (US); Andy Eow, Brooklyn, NY (US); Xiaoxu Ma, Sunnyvale, CA (US)

(73) Assignee: NetVirta, LLC, Norwell, MA (US)

(*) Notice: Subject to any disclaimer, the term of this patent is extended or adjusted under 35 U.S.C. 154(b) by 86 days.

(21) Appl. No.: 12/864,870

(22) PCT Filed: Jan. 28, 2009

(86) PCT No.: PCT/US2009/000560
§ 371 (c)(1),
(2), (4) Date: Jul. 27, 2010

(87) PCT Pub. No.: WO2009/097122
PCT Pub. Date: Aug. 6, 2009

(65) Prior Publication Data
US 2010/0319100 A1    Dec. 23, 2010

Related U.S. Application Data

(60) Provisional application No. 61/023,931, filed on Jan. 28, 2008, provisional application No. 61/029,601, filed on Feb. 19, 2008.

(51) Int. Cl.
*G06F 19/10*    (2011.01)

(52) U.S. Cl.
USPC ........................................................ 700/135

(58) Field of Classification Search
USPC .......... 700/118, 131, 132, 130, 135; 382/111, 382/108, 195, 204
See application file for complete search history.

(56) References Cited

U.S. PATENT DOCUMENTS

| | | | | |
|---|---|---|---|---|
| 4,885,844 A * | 12/1989 | Chun | ................................ | 33/15 |
| 5,163,006 A * | 11/1992 | Deziel | ........................... | 700/132 |
| 5,956,525 A * | 9/1999 | Minsky | .............................. | 396/3 |
| 6,101,424 A * | 8/2000 | Sawada | ......................... | 700/136 |
| 6,473,671 B1 * | 10/2002 | Yan | .............................. | 700/134 |
| 7,489,813 B2 * | 2/2009 | Rutschmann et al. | ........ | 382/154 |
| 2001/0026272 A1 * | 10/2001 | Feld et al. | ...................... | 345/419 |
| 2004/0104935 A1 * | 6/2004 | Williamson et al. | .......... | 345/757 |
| 2004/0258309 A1 * | 12/2004 | Keaton et al. | .................. | 382/190 |
| 2006/0221072 A1 * | 10/2006 | Se et al. | ........................ | 345/420 |

FOREIGN PATENT DOCUMENTS

DE    19502459 A1 *    8/1996

* cited by examiner

*Primary Examiner* — Danny Worrell

(57) ABSTRACT

Techniques which employ structure-from-motion modeling techniques to produce 3-D models of any desired accuracy of any surface I the techniques, a pattern is applied to the surface to be modeled The pattern includes elements which are unique within the pattern as applied to the surface and which have a density in the pattern such that when two-dimensional images are made of the surface, correlatable features having the density required for the desired accuracy may be extracted from the two dimensional images In one example of the techniques, a consumer may make the images required to produce a model of his or her body by donning a garment with a pattern having the necessary uniqueness and density, and then using any digital camera to take pictures of their body wearing the garment The model may then be produced from the pictures.

31 Claims, 12 Drawing Sheets

Overview of operation

Overview of operation

Extraction and correlation of features

301 — Feature ID
303 — Body Part
305 — Color 1 / Color 2 / ... / Color n
307 — Feature ID Top / Feature ID Left / Feature ID Right / Feature ID Bottom
309 — ...

300
Feature Reference Table Entry

351 — Feature ID
353 — Image ID
355 — X Position / Y Position
357 — ...
365
363
361

350
Correlation information for a feature

Data structures used in correlation
Figure 3

400

410

Example of garment with pattern

Individual wearing garment for images

600

Wire Frame Model

Using the Garment

Examples of preferred patterns

Examples of reference objects

Examples of posing aids

Embodiment using a web-cam camera

Overview of
Feature extraction, correlation, model construction

SIMPLE TECHNIQUES FOR THREE-DIMENSIONAL MODELING

CROSS-REFERENCE TO RELATED APPLICATIONS

The subject matter of this patent application is related to and claims priority from the following U.S. patent applications, each of which is hereby incorporated by reference in its entirety:

U.S. Provisional Patent Application 61/023,931, Jian Chen, et al, Simple Apparatus for 3-D Reconstruction of Human Bodies, filed Jan. 28, 2008.

U.S. Provisional Patent Application 61/029,601 Jian Chen, et al, Simple Apparatus for 3-D Reconstruction of Human Body Parts, filed Feb. 19, 2008.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

This invention relates to techniques for extracting information from and producing models of a three-dimensional surface. Applications of the techniques include producing models of parts of a human body. The models may be used to select sizes of ready-made clothing or to make custom-made clothing.

2. Description of Related Art

There are many known ways of making mathematical models of three-dimensional surfaces. There are many possible applications for these techniques; however, these techniques are too difficult and/or expensive for ordinary consumers to use them for making accurate three-dimensional models, and thus too difficult or expensive to be used in application such as selecting or fitting clothing.

Problems in Modeling the Shape of Objects Such as the Human Body

Modeling the shape of an object, such as a part of a human body as may be done for the fitting of clothing, is a difficult problem. Many of the difficulties of the problem lie in the nature of the existing techniques for modeling the shape, in the nature of the human body, and in the nature of clothing, and include the following:

- Human bodies are not standardized.
- Determining an accurate model for the shape, such as for custom-sized and fitted clothing, requires extensive measurements.
- Existing techniques are expensive, awkward, inaccurate, and inconvenient for consumers to perform.
- Standard sizes of clothing are based on models that are not accurate for most wearers of the clothing.

To illustrate the difficulties, an expert seamstress or tailor making or fitting a garment makes a number of measurements of parts of an individual's body. Effectively, the seamstress makes a model of the individual's body parts; the seamstress may also create a physical model in the form of an adjustable seamstress's dummy from the measurements by adjusting the dummy according to the measurements. The seamstress's dummy is a physical model that is adjusted to reflect a mathematical model determined by the measurements. Even so, the clothing must be altered to fit on the actual individual, because the model is not sufficiently accurate.

Current Techniques for Constructing Models of Parts of the Human Body

Automated systems exist for producing measurements of parts of the human body.

Laser Body-scanning

A number of specialized systems in the area of tailoring exist that take measurements of a human body or parts using laser body-scanning. In these systems, the individual to be measured goes to a special facility to pose for measurement. At the facility, a highly precise light source, such as a safe laser light, is used to project a number of illuminated traces across the body in a precisely-known set of paths. The locations where the light of the traces is reflected from the surface constitute a set of precisely-located reference points upon which measurements relevant to the surface can be based. Digital cameras or other optical viewing sensors which are calibrated and located at precisely-known positions detect the laser light reflected from the individual's body where the light strikes the individual's body, and determine the viewing location of the trace paths as the light illuminates the traces. Using a mathematical process such as triangulation, this location information, along with the precise positions of the light source and of the camera, is processed to calculate the actual path locations on the surface of the individual's body and to produce a mathematical model of the surface of the individual's body.

Exemplary systems of this kind include Intellifit, intellifit.com/fitting_process and TC2, tc2.com/products/body_scanner.html. (References fetched from the World Wide Web on Jan. 10, 2009)

Disadvantages of these kinds of systems include the following:

- The systems require special equipment that must be calibrated precisely.
- The systems cannot be used in the consumer's home environment.
- The systems are invasive: consumers need to wear minimum clothing in a semi-public setting.
- The use of lasers in the technology may give users a perception of physical risk.

Key-in Measurement Systems

There are systems in which an individual takes measurements manually and the measurements are submitted electronically to a system that computes a three-dimensional model from the measurement data. These systems fall into two classes: those used to fit custom-made haute couture clothing, and those for consumer use at home The haute couture systems require the kinds of measurements made generally by expert seamstresses for custom clothes; they merely automate the process of making the model from the measurements.

With home systems, the consumer, perhaps with the assistance of a person of her or his choice, makes measurements of the individual's body. The measurements are made at home, using a set of instructions. The consumer then inputs the values of the measurements to an electronic form, such as a Web page form, and the values are submitted to a system that computes a three-dimensional model for the shape of the individual's body part from the measurement data. The model may then be used to obtain clothing made or fitted according to the three-dimensional model.

Exemplary systems of this kind include MyShape, myshape.com, and My Virtual Model, myvirtualmodel.com/en/index.php. (References fetched from the World Wide Web on Jan. 10, 2009)

Difficulties with such consumer systems include:
The individual measurements made by consumers are not sufficiently accurate.
Making the many measurements themselves is laborious for the consumer. It is further laborious to submit all the measurements manually by typing them into the electronic form.
The process for submitting data is subject to data-entry errors.
It is not possible to get either a sufficient number of measurements or many special measurements that may be required.

Feature-based Modeling:

Feature-based modeling has been used to produce models of surfaces. Feature-based modeling produces a three-dimensional model of a surface from a set of two-dimensional images of the surface. The feature-based modeling system extracts features from the images. A feature represents an element of the surface which appears in an image belonging to the set of images. The feature specifies the location in the image at which the element appears. If a particular element appears in more than one image, a feature can be extracted for each of the appearances. The feature-based modeling system can use the different locations of the features in the images belonging to the set of the images to make the three-dimensional model of the surface. The operation of determining that more than one feature represents a particular element of the surface which appears in the images of the set of images is called correlating the features. An example of a system using the techniques of feature-based modeling is a computer vision system. Two general references to computer vision systems are "Computer Vision: A Modern Approach", by David A. Forsyth and Jean Ponce, Prentice Hall, 2002, and "Multiple View Geometry in Computer Vision., $2^{nd}$ Edition", by Richard Hartley and Andrew Zisserman, Cambridge University Press, 2004. Kinds of feature-based modeling include stereo vision, which requires cameras that are precisely-calibrated for viewing angles, rotation and location to construct three-dimensional models using correlated features, and structure-from-motion, which does not require calibrated cameras to construct three-dimensional models using correlated features.

Feature-based modeling has also been applied to making dynamic models of objects and to motion capture of human bodies. An exemplary reference is "Uncalibrated Motion Capture Exploiting Articulated Structure Constraints", David Lebowitz and Stefan Carlsson, Eighth IEEE Conference on Computer Vision 2001, Vancouver, British Columbia.

Production of a model of a surface from a set of images of the surface being modeled involves the following steps in both stereovision and structure-from-motion:

Images: A number of two-dimensional images from a variety of viewing angles of the surface are obtained.
Feature extraction: Features are extracted in each of a number of the two-dimensional images.
Feature correlation: The same features are identified and matched in multiple two-dimensional images. Another term for feature correlation is feature matching.
Model computation: Using information about the positions of correlated features in the images, a three-dimensional model of the surface is computed.

Additional steps may be employed, such as a step of processing the image or information of the image, to improve the quality of the features.

To date, a serious limitation on the use of stereo vision to make models of surfaces is the need for precise calibration of one or more cameras with regard to location and orientation relative to the surface being modeled and also with regard to the camera's focal length, if an accurate model is to be produced from the correlated features. One reference that discloses the mathematics of camera calibration for stereo vision is "A Versatile Camera Calibration Techniques for High-Accuracy 3D Machine Vision Metrology Using Off-the-shelf TV Cameras and Lenses", IEEE Journal of Robotics and Automation, Vol. RA-3, NO. 4, August, 1987.

A serious limitation to date on the use of structure-from-motion to make models of surfaces is that enough elements of the surface being modeled must appear in the images being used to make the model to permit the extraction of enough correlatable features to provide a density of correlated features which is sufficient to produce a model having the accuracy required for the model's intended applications. The human body is an example here: the surface of the human body ordinarily does not have enough elements which appear in images of the human body to permit extraction of enough correlatable features to permit construction of models of the body which are accurate enough to be used in fitting clothing.

OBJECT OF THE INVENTION

It is an object of this invention to address these problems of the existing art by providing techniques for producing images of three-dimensional surfaces which do not require precise camera calibration and can provide a density of elements in the images such that any required density of correlatable features may be obtained from the images.

BRIEF SUMMARY OF THE INVENTION

In one aspect, an object of the invention is achieved by a method of obtaining a set of images from which a three-dimensional model of a surface may be made which has the following steps: A pattern is applied to the surface to be modeled. The pattern which is applied to the surface includes pattern elements that have a uniqueness within the surface to be modeled. After the pattern has been applied, a set of images of the surface is made. The pattern's elements are perceptible in the images. Features needed to make the model are extractable from the perceptible pattern elements. The uniqueness of the perceptible pattern elements makes the features extracted from them correlatable. The density of the extractable features is determined by the density of the perceptible pattern elements in the images.

Another aspect of the invention is a method of making a three-dimensional model of a surface from images which have been made as just described. The steps of the method are extracting the features needed to make the model from the perceptible pattern elements, using the uniqueness of the perceptible pattern elements to correlate the extracted features, and using the correlated extracted features to make the three-dimensional model.

Still another aspect of the invention is a covering which has the kind of pattern just described and is conformable to the surface being modeled. When the covering has been conformed to the surface, a set of images may be obtained as described above and the model may be made from the images. The covering may be a component of a kit for making models.

One area of application for the techniques is obtaining models of portions of the human body. In this area of application, the covering is a garment which has the kind of pattern just described and is worn over the portion of the body for which the model is being made.

Upon perusal of the Detailed Description and Drawings below, other objects and advantages will be apparent to those skilled in the arts to which the invention pertains.

BRIEF DESCRIPTION OF THE SEVERAL VIEWS OF THE DRAWINGS

FIG. 3 shows data structures used in the extraction and correlation of features

Figure 1:
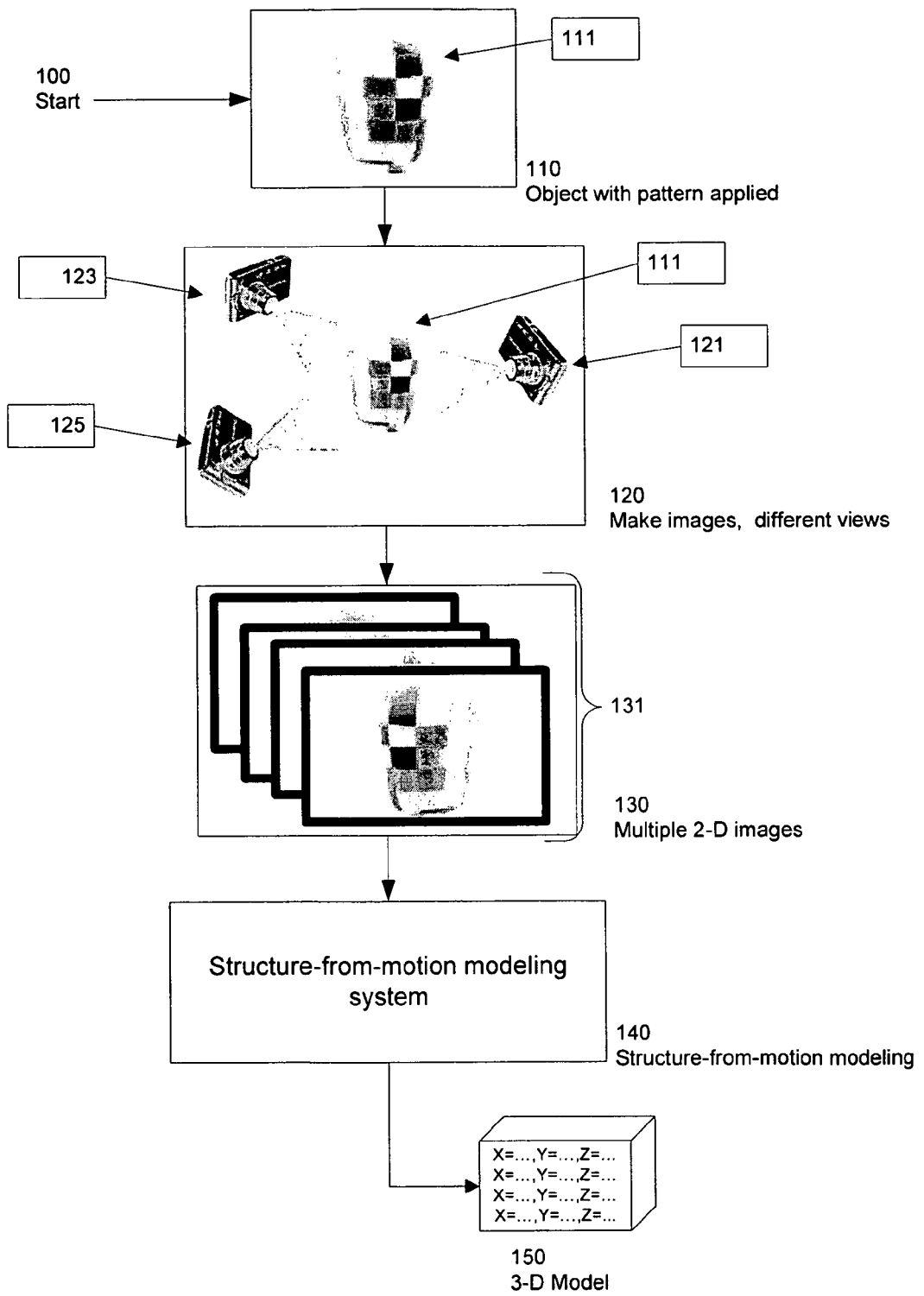
FIG. 1 shows an overview of the operation of the preferred embodiment.

Reference numbers in the drawings have three or more digits: the two right-hand digits are reference numbers in the drawing indicated by the remaining digits. Thus, an item with the reference number 203 first appears as item 203 in FIG. 2.

DETAILED DESCRIPTION OF THE INVENTION

The following Detailed Description of the invention first provides a broad overview of the inventive techniques. The Detailed Description then discloses an embodiment used to make models of parts of the human body for use in fitting clothing.

Overview of the Inventive Techniques

The techniques of this invention provide a solution to the problem of making a three-dimensional model of a surface when a particular accuracy is required for the model and the surface does not have enough elements which appear in images of the surface to permit extraction of enough correlatable features from the images to provide the density of correlatable features needed for the required accuracy.

This problem is solved by applying a perceptible pattern to the surface for whose shape the three-dimensional model is to be made. The pattern provides enough extractable features for the application, and further provides features such that they can be correlated readily using uniqueness of elements in the pattern within the surface for which the model will be made. In this context, a pattern element with uniqueness within a surface is any portion of the pattern that is unique within the surface. The pattern may be applied by any convenient means, including but not limited to painting the surface with the pattern, projecting the pattern onto the surface, or covering the surface with a covering that has the pattern.

The foregoing technique may be used with any feature-based modeling technique to increase the density of the features beyond what would otherwise be available from images of the surface.

FIG. 1 illustrates techniques of this invention in a graphical flowchart overview, starting at 100.

110 shows the first step of applying the pattern to the surface. The exemplary object is at 111 as a rounded medium-tall object with the covering. The pattern in the illustration is composed of solid rectangles of different colors in a grid arrangement. The pattern is sufficiently unique that the required correlatable features can be extracted from an image of the covered object and sufficiently dense that structure-from-motion modeling can produce a model of the surface of the object which has the required accuracy.

120 shows the step of making two-dimensional images of the object 111 with the pattern in different views. 120 shows three illustrative views 121, 123 and 125 being taken by a camera. The images are taken from a number of different angles or points of view, as illustrated at 120. Because structure-from-motion is being used to make the model, the subsequent step 140 requires no special calibration of the camera as regards location and orientation relative to the surface or as regards the camera's focal length.

130 illustrates that a number of two-dimensional images 131 have been acquired. Each of the images shows a different view of the object with the covering. The images are then provided to a structure-from-motion modeling system: an example is a computer system that is programmed with software to apply algorithms of structure-from-motion to create a three-dimensional model of the surface from information in the images.

140 is the step performed by the structure-from-motion modeling system. The system executes software that uses algorithms to extract and correlate features, and uses algorithms of structure-from-motion to produce a mathematical three-dimensional model 150 of the surface, from the multiple two-dimensional images of the surface with the covering. The structure-from-motion modeling system is described above. The implementation for feature extraction and correlation is described below for FIG. 2. The output of 140 is illustrated at 150.

Figure 6:
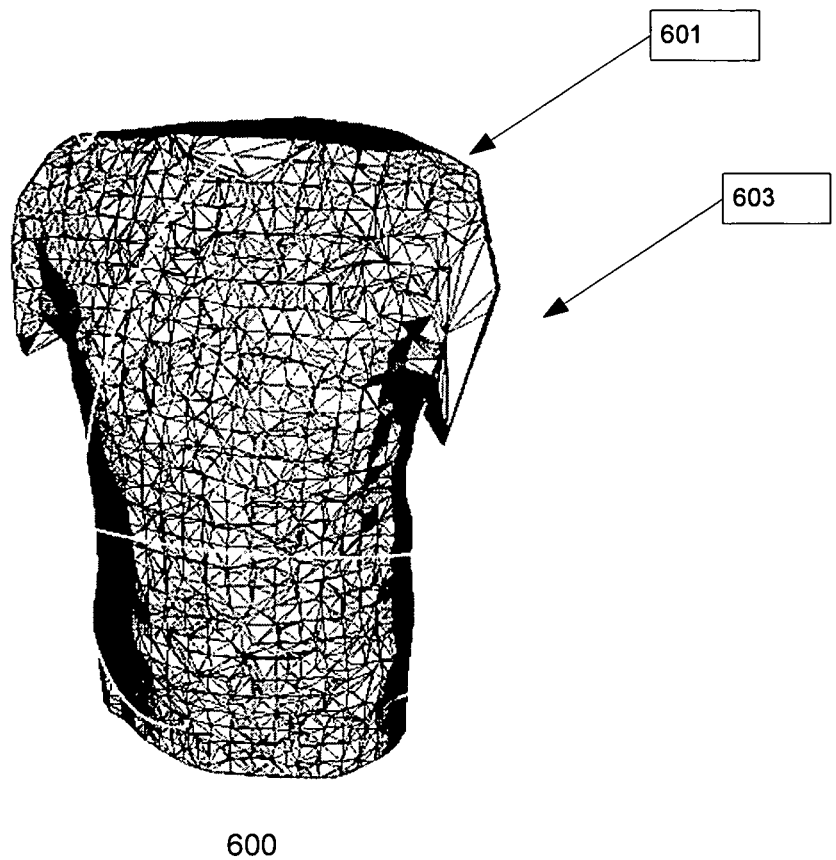
FIG. 6 shows an exemplary wire frame model produced using the garment.

150 represents the mathematical model that is the result of the step at 140. The form of the mathematical model depends on the implementation of structure-from-motion employed in implementing step 140: one form is a set of (X, Y, Z) three-dimensional coordinates for the model of the surface. The mathematical model may be represented in wire-frame form: a wire-frame model is a mathematical model in which points that are adjacent on a mathematical surface are connected by line segments. An illustration of a wire-frame model for a different object is shown in FIG. 6.

Models may be static models, or dynamic models. Static models do not represent a moving surface. Dynamic models do represent a moving surface: motion of the surface may be represented for example by change vectors, or by a series of static models representing the surface at sequential moments in time.

A model may be a sub-model of another model. For example, in the preferred embodiment there may be a model for the shape of the torso or the left arm, and these both may be sub-models of a model for the entire upper body. Where a model includes submodels, the perceptible pattern elements need be unique only with respect to the submodel.

A model may be constructed for any physical object, such as a mechanical part that must be replaced or an object of art, and the model used to construct a physical replacement for the mechanical part or a copy of the object of art. The model may also be used to produce a copy of an object at a different physical scale, such as a smaller replica of an object of art, or as part of a process to produce a modified version of an object, such a replica of a statue in which parts of the statue have been modified but other parts retain fidelity to the original object. Objects may be modeled in situ by employing a covering of the kind of this invention, such as large objects that cannot easily be moved or transported so that they can be examined or measured: these may be objects of any sort, including large or small archeological objects, large or heavy equipment, or architectural objects.

As one example, a model may be used to create input for three-dimensional printer to products copies of objects, statues at large or small scale of an actual person, customized awards and plaques, or other objects.

Overview of Correlation with Examples of the Preferred Embodiment

Figure 2:
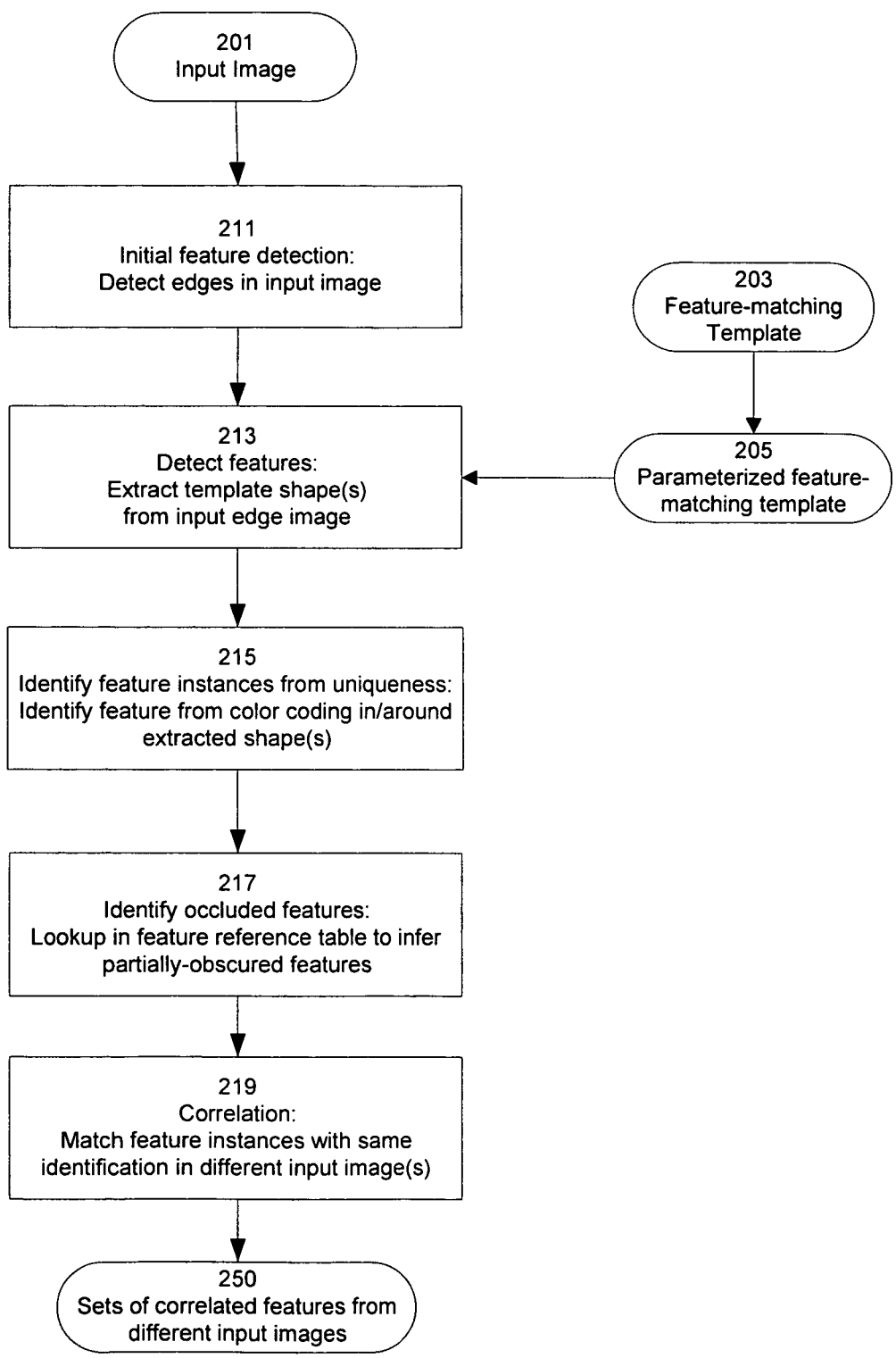
FIG. 2 is a flowchart for extraction and correlation of features in the preferred embodiment.

FIG. 2 is a flowchart for the techniques used for feature extraction and correlation in step 140 of FIG. 1. The description makes reference to examples of the preferred embodiment: these examples are not limiting.

Processing starts at a 201 with an input image from the set of step 130 of FIG. 1.

Step 211 shows the step of performing initial feature detection on the image. In this context, initial feature detection is a process that extracts information from an image so that the features employed in constructing a model can be detected. There are many possible techniques of initial feature detection that may be employed. For example, the preferred embodiment employs edge detection, such as the known techniques of Sobel edge detection and Canny edge detection. Techniques to improve the quality of the image that also preserve the information of initial feature detection may also be employed in this step, such as a smoothing-filter operation to reduce the amount of noise in the image.

At step 213, the features that may be employed in construction a model are detected. In the preferred embodiment a feature-matching template method is used to detect features in the image. As shown at 203 and 205, in the preferred embodiment well-defined shapes are used as templates, and features are extracted using known techniques such as the Hough Transform. The pattern and the templates in the preferred embodiment are chosen together to optimize overall performance. 205 indicates that the templates may be parameterized so that any type of pattern may be used, such as one with arbitrary elements such as trademarks, logos, and graphical symbols.

At step 215, the individual feature instances detected in step 213 are identified using the uniqueness of elements in the pattern on the surface for which the model will be made. For example, in the preferred embodiment colored components of the elements in the patterns of the preferred embodiment are matched to combinations specified in entries in a feature reference table, as illustrated at 300 in FIG. 3. When the colored components of an element match the combination of colors of the feature reference table entry, the feature instance corresponding to the element is assigned the Feature ID value in the entry.

217 shows an optional step of using the uniqueness of a larger pattern which includes a smaller portion whose uniqueness cannot be determined in the image to identify the smaller portion. This problem can arise when a part of the pattern is not visible in the image. The pattern that is not visible is then said to be occluded. In the example of the preferred embodiment, part of the view of an element on the torso may be blocked by the individual's arm. If features immediately next to the partially obscured feature are identified, the pattern of the preferred embodiment is such that the partially-obscured feature is identified by knowing the features it is near. This is described below for the corresponding data structure at 300 in FIG. 3.

219 shows the step of correlation, which matches the same identified features in several images. The output of this step is sets of correlation information for each identified feature, shown at 250. 250 is the output of the process of extracting and correlating features, and is the information processed by techniques of structure-from-motion to produce the model. In the preferred embodiment, correlation is done by matching the same identified features in several images, by a global search across several images. This is described in the context of the preferred embodiment for 350 in FIG. 3.

Examples From a Preferred Embodiment

FIG. 3 describes two data structures of the preferred embodiment mentioned in the description of FIG. 2.

300 illustrates an entry in the feature reference table of the preferred embodiment.

301 is labeled Feature ID, a unique key identifying the feature of this entry in the table.

303 is labeled Body Part. In the preferred embodiment of the garment there may be different patterns for the parts of the garment that cover particular parts of the body. The different parts of the body are modeled as submodels of the entire body. Where this is done, a pattern element needs to be unique only within the pattern for the submodel. The Body Part 303 is an identifier that indicates the body part where this feature may appear: e.g. torso, left leg, right arm, left pinky finger according to the particular form of the garment. The identifier thus serves to identify the submodel to which the pattern applies.

305 is a set of values stating the combination of colors that appear in components of the element for the particular feature corresponding to the Feature ID value of 301.

The values at 307 are the Feature ID values for features that are near the feature of Feature ID 301. In this illustration the locations of elements from which features are extracted in the pattern correspond to an approximately rectilinear arrangement: the four nearby features are identified conveniently as being to the top, right, left, or bottom of the feature of this entry.

309 indicates that further information may also be included in the entries of the feature reference table, according to the particular application.

350 illustrates a set of correlation information for a feature, as described at 250 in FIG. 2. 361 and 363 show records for a feature that has been correlated for two images: 365 indicates that the feature may be correlated for additional images as well. Each record in the set corresponds to the same feature instance, and thus has the same Feature ID value 351.

351 and 353 identify a feature, and an image in which it appears, respectively.

355 shows two values, for the X and Y positions of the feature 351 in the particular image 353.

Figure 12:
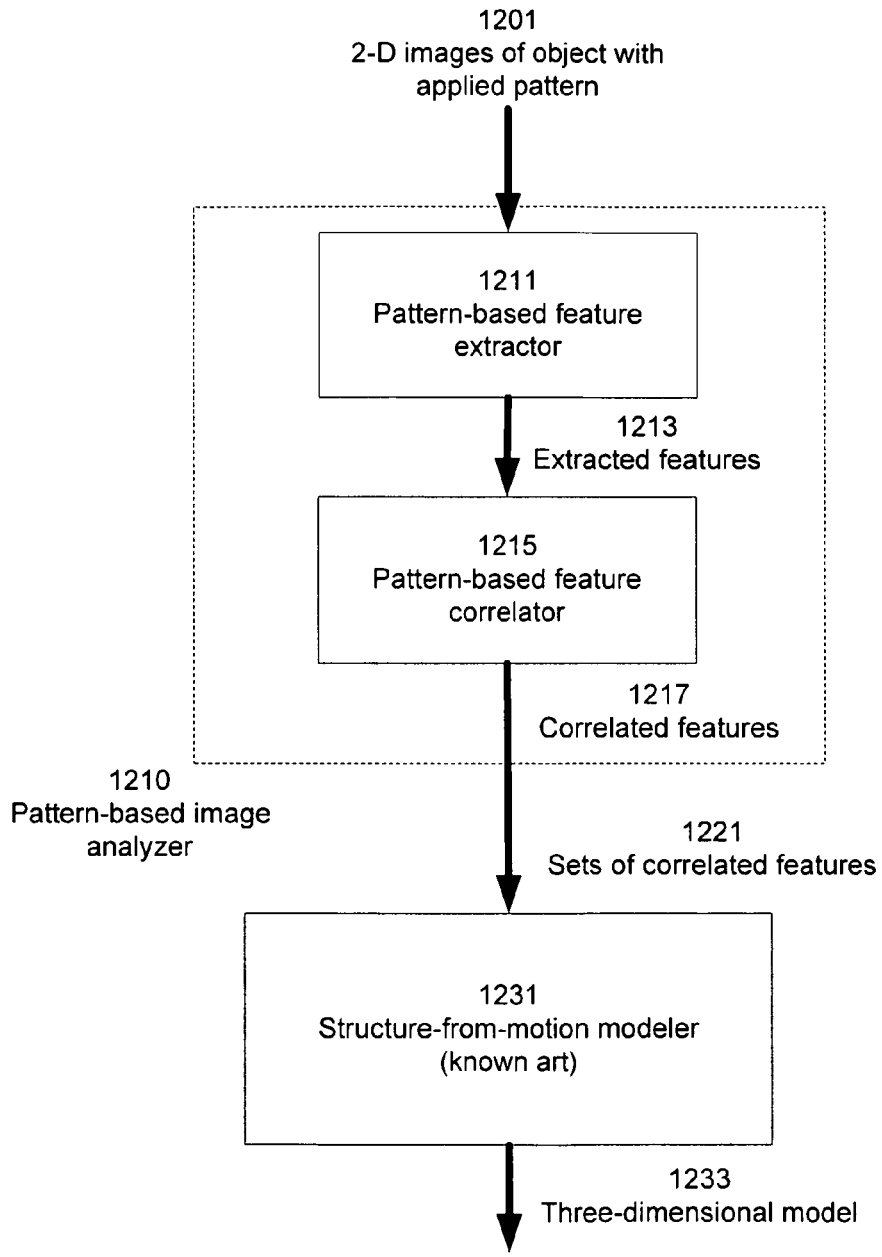
FIG. 12 shows the relationship of components for feature extraction, correlation, and model construction in the preferred embodiment.

FIG. 12 illustrates the implementation relationship in the preferred embodiment for the software components for feature extraction, for correlation, and for construction of the model. 1210 shows that the feature extraction and correlation software implementation can be considered collectively to be a pattern-based image analyzer. The input to the pattern-based image analyzer 1210 is a set of two-dimensional images of the surface with the applied pattern, also referred to at 201 in FIG. 2. The output of the analyzer 1210 is set of correlated features, also shown at 250 in FIG. 2.

Describing the internal implementation of the analyzer 1210, 1211 shows that the implementation contains a first general component referred to here as a pattern-based feature extractor. The input to this component is a set of two-dimensional images of 1201. The output is the features that have been extracted 1213. This output in turn is the input to a second general component 1215, referred to here as a pattern-based feature correlator. The output of 1217 is a set of features that have been correlated for multiple input images of 1201.

The output of the general component of the analyzer 1210 is sets of correlated features, as shown for output at 1221. This is input to 1231, referred to here as a structure-from-motion modeler, and labeled as known art: techniques for structure-from-motion modeling from sets of correlated features of sufficient density and quality are described in the references to computer vision. The output of the modeler 1231 is shown here as the constructed three-dimensional model of the surface 1233. Output of analyzer 1210 could also be provided to any kind of modeling system in which the correlated features would be useful. The output could be used, for example, to increase the accuracy of models produced by a stereovision system.

Overview Of The Preferred Embodiment

The preferred embodiment is a system for making three-dimensional models of parts of the human body. The pattern needed for feature extraction and correlation is applied to the body by providing a garment with the pattern to the person of whose body the model is being made. The garment is constructed to conform to the shape of the surface of a part of the individual's body. The garment is used in making the model as follows:

The individual puts on the garment on the part of the body to be modeled.

Using an ordinary digital camera, a number of two-dimensional images are taken of the user wearing the garment with the pattern, from a number of different angles. Because structure-from-motion is being used to do the modeling, no special care is needed in taking the images.

The images are provided to a structure-from-motion modeling system for constructing a model.

A structure-from-motion modeling system extracts features from the pattern in the images, and correlates the features in a number of images.

The structure-from-motion system constructs a three-dimensional model of the part of the body covered by the garment, using information of the surface from these features.

Figure 4:
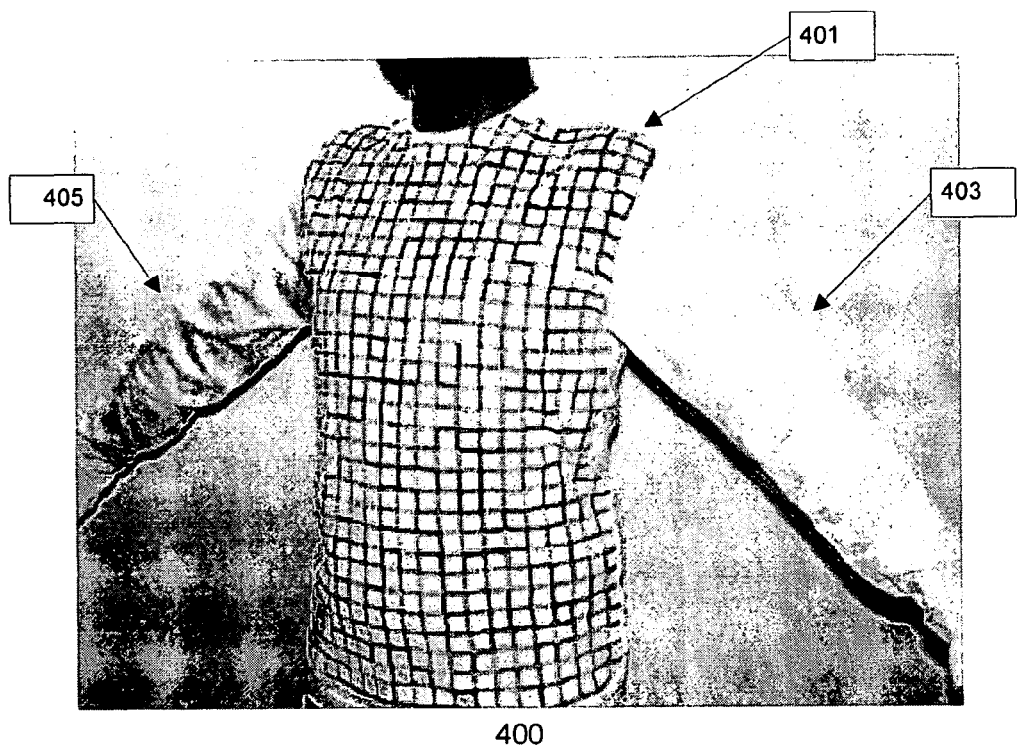
FIG. 4 shows two examples of the garment with a preferred embodiment of the pattern.
Figure 4:
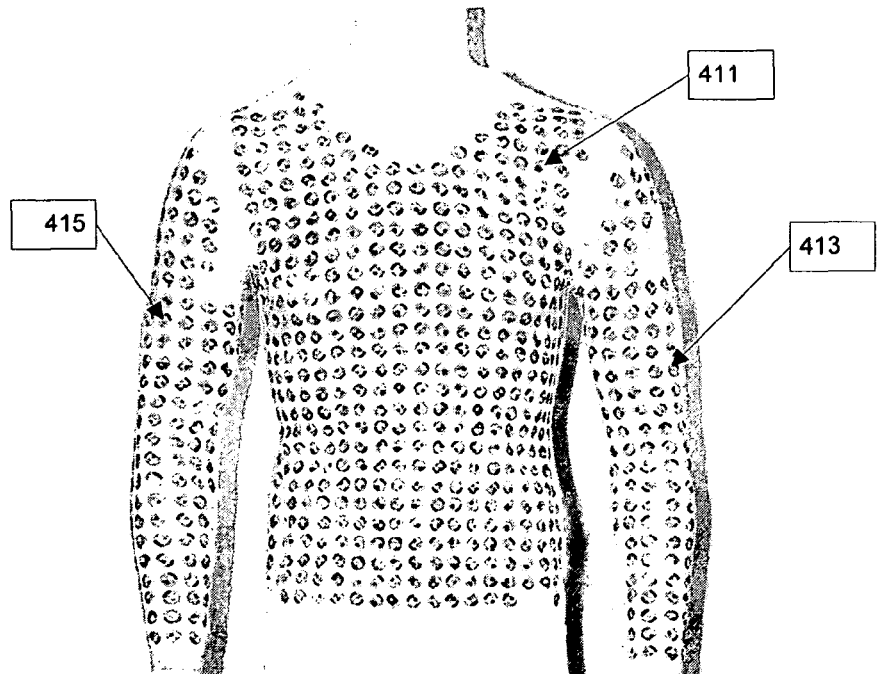

FIG. 4 shows two example forms of a presently-preferred embodiment of the garment and its pattern. 400 shows one form of the patterned garment. The garment covers and conforms to the torso 401: this particular form of the garment is made of material that conforms sufficiently to construct models for fitting of "comfortable fit" clothing. The individual is posing with the arms held away from the body at 403 and 405, so that images can be made of the garment from different angles. 410 shows a second form of the garment 411, with the pattern also covering the arms, as shown at 413 and 415. The form of the garment shown at 410 is made of a more conformable material such as spandex.

Figure 5:
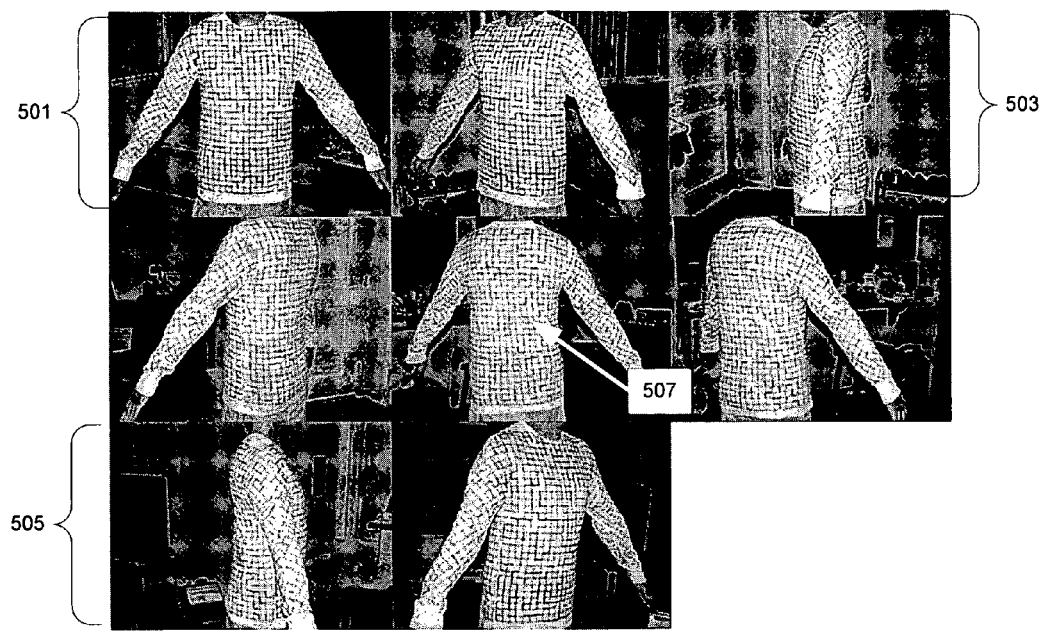
FIG. 5 shows several views of an individual wearing the garment for images.

FIG. 5 illustrates the individual wearing a form of the preferred-embodiment garment covering both torso and arms, and posing similarly to 400 in FIG. 4 while images are made with the camera. 501, 503, 505, and 507 show poses for images from angles for the front, left, right, and rear sides respectively. Also shown are poses for angles between these angles. The garment with the pattern in this example also covers the arms.

FIG. 6 shows a wire-frame illustration of the three-dimensional model constructed from information about the features extracted from the images. The model represents a model made with the garment of 400 in FIG. 4, in which the garment with the pattern covers the torso, as shown at 601. The model does not include the surfaces of the sleeves or arms, as is shown at 603.

Advantages of these techniques for obtaining a model of parts of the human body for fitting clothes include:

Low cost.

The only special item used is the garment with the pattern. This can be produced very cheaply, and can be made such that the garment is disposable after use.

Easy to manufacture and provide.

The garment can be made of ordinary clothing materials by ordinary production means for garments. The garment can be provided to the consumer by ordinary mail or other means.

Easy for ordinary consumers to use.

Operation is simple and requires no special expertise or training. The images can be taken with a consumer-grade digital photographic camera, such as the consumer is likely to have available. The angles for the images, and the positions of the camera and of the individual, need neither be calibrated nor pre-determined. Images can be easily provided to a computer for producing the model.

May be used in a consumer's home environment with little or no assistance.

Robust and reliable results.

The models are very accurate and detailed.

Details Of The Presently-preferred Embodiment

In a presently-preferred embodiment, the garment is in the form of a long-sleeved shirt for making models of the torso, shoulders and arms of a human body. The garment is made of a snug, close-fitting material with sufficient stretchiness to fit closely to the body, shoulders and arms when worn by individuals of a range of sizes. Spandex is a suitable material for the garment, but other materials may be used: an example of a garment made from a material like spandex is shown at 410 in FIG. 4. The sleeves may be omitted from the garment if no modeling of the arms is required by the application. A garment may also be constructed equivalently for any part of the body.

Using the Garment

Figure 7:
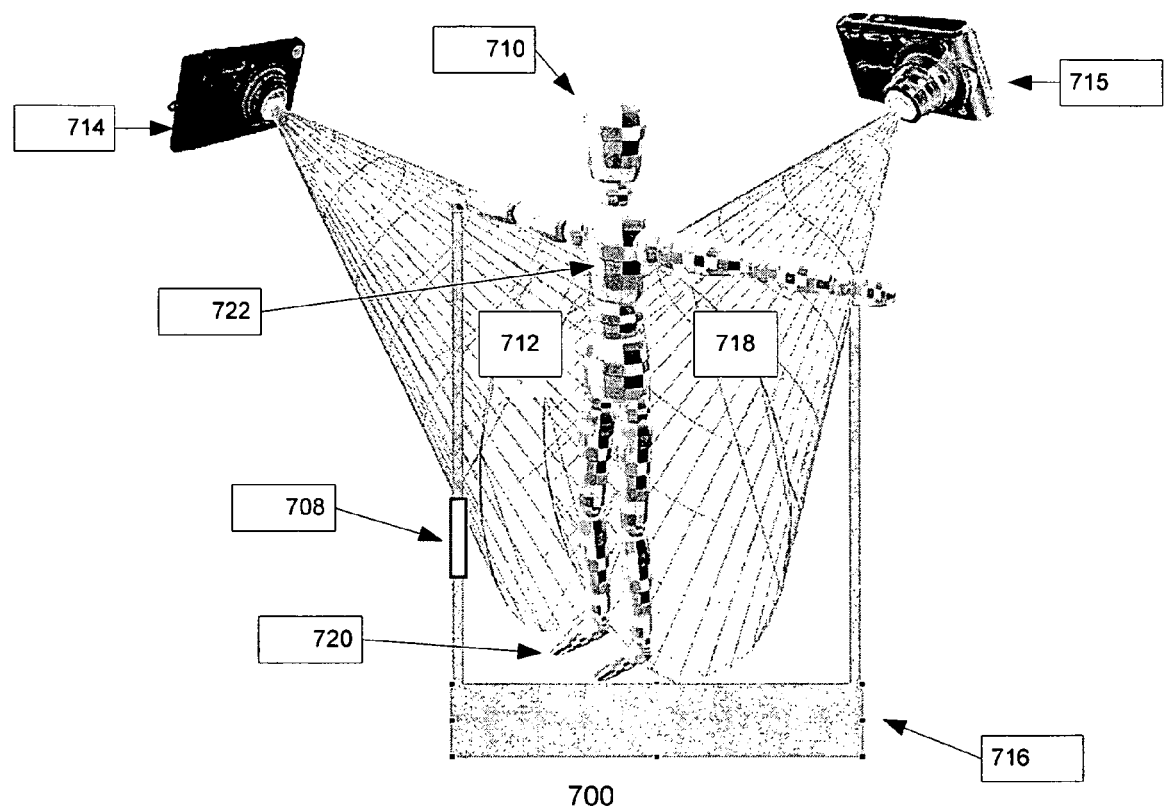
FIG. 7 illustrates the use of the garment in the preferred embodiment.

FIG. 7 illustrates details of the using the garment of the preferred embodiment.

The human figure at 710 represents an individual wearing a garment. For purposes of illustration, the human figure is shown with the garment covering the entire body. The two camera images labeled 714 and 715 represent images being made from different angles 712 and 718 of the individual wearing the garment. 716 is an optional physical aid: a stand to help support the individual's arms while posing, described below. 708 is an optional reference object aid, in this example combined with the physical aid 716, to assist in determining dimensional scale in the images and dimensional scale in the model. The pattern at 720 has a pattern of greater density on the feet: this part of the body has greater curvature than the torso 722, and the greater pattern density is needed to model the curvature of the feet accurately.

The garment may be in any convenient form, and may cover multiple parts of the human body. For example, the garment may be in the form of a body-stocking garment. This kind of form for the garment may be especially convenient for certain kinds of applications, such as one in which the individual uses the garment in a dressing room in a store. The garment may be produced in whole or in part in any convenient fashion, such as on demand. For example, the garment may be printed in sections when needed on a computer printer available to the individual, and the sections combined.

Examples of the Pattern

Figure 8:
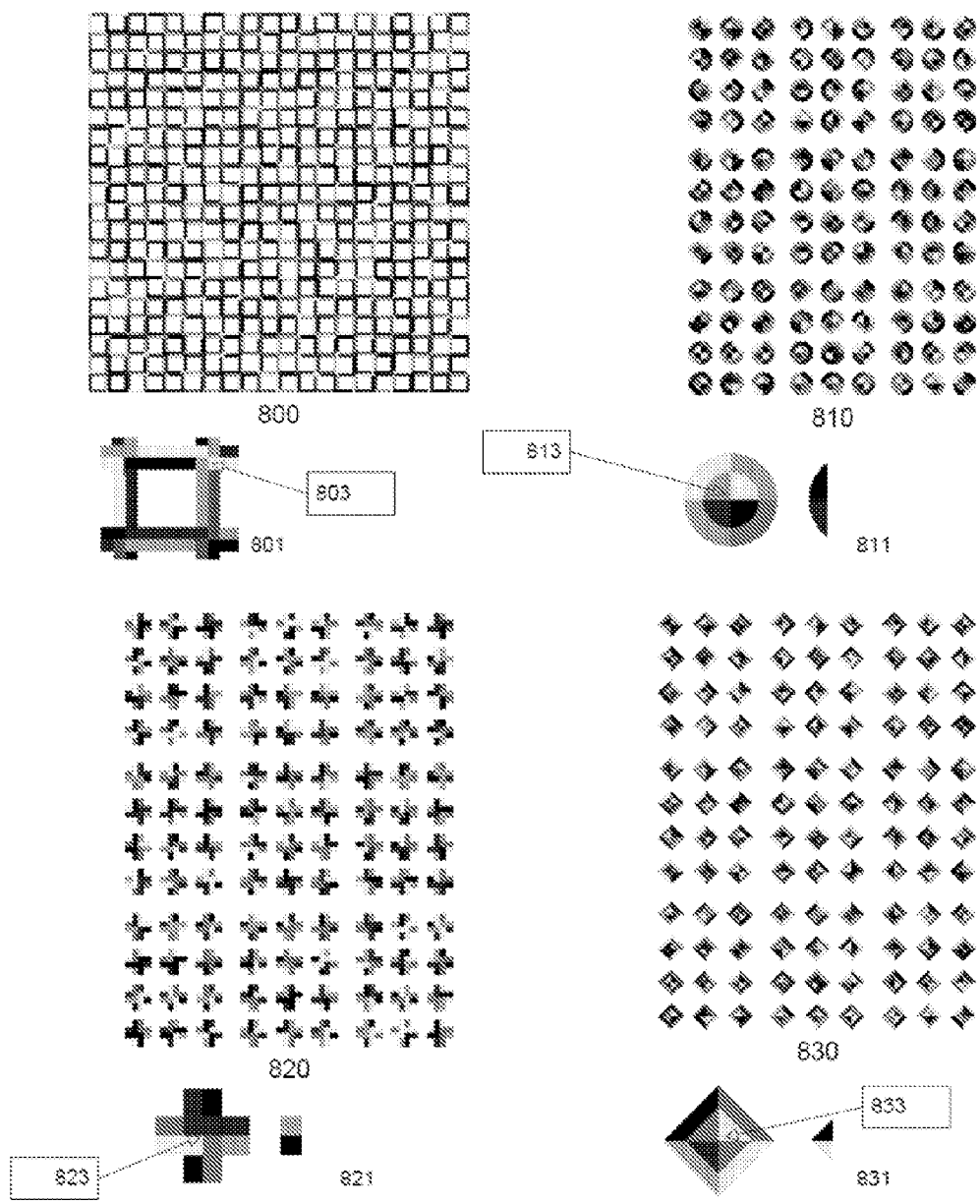
FIG. 8 shows examples of patterns of the preferred embodiment.

FIG. 8 shows a number of examples of patterns employed for the presently-preferred embodiment of the garment. Four examples of patterns are shown: 800, 810, 820, and 830. Enlarged views of details of the patterns are shown respectively at 801, 811, 821 and 831. The patterns shown at 810, 820, and 830 are each composed of a more-or-less regular mesh arrangement of elements defined by geometric shapes with colored components. The combination of colors in the colored components of a pattern element is unique within the model (which may be a submodel) and provides the uniqueness needed to correlate the features extracted from different images. There is however neither any requirement that a pattern be composed of similar geometric elements, nor that any part of the pattern have a regular arrangement, nor that the pattern contain specific elements which are unique in themselves: the only requirement is that features can be extracted of sufficient density for producing the model, and that the extracted features can be correlated from the pattern elements that appears in the images. In the example patterns of FIG. 8, the extracted features can be correlated from the combinations of colored components which are associated with the features. The combinations are unique to an area of the garment which covers a part of the body for which a submodel is being made.

In the presently-preferred embodiments of the pattern, a density of the extracted features of not less than one feature instance in a linear distance of three centimeters has been determined to be a useful density for modeling the human torso for the fitting of clothes. In the preferred embodiment, a higher density, such as a density of one feature instance in a linear distance of one centimeter, may be useful for other parts of the body. The pattern may differ on different parts of the garment. Patterns for which the features obtained have differing feature density may be used in different parts of the garment. For example, a greater density may be employed where the garment covers a part of the body where the surface has greater local curvature than another, such as for the case of the arms and torso, the surface of an arm generally having greater local curvature than does the surface of the torso.

The pattern of 800 is composed of a grid of lines, colored in line segments forming squares. In the preferred embodiment, features are extracted from the intersections of the line segments: the location of the feature in the model is determined from the location of the intersection in the correlated images. 801 shows an enlarged view of part of the pattern: 803 indicates an instance of an element of the pattern: the arrow of 803 points to the intersection of the line segments.

The pattern of 810 is composed of elements that are non-overlapping circle shapes. The circled shapes are composed of arc line segments divided into colored quadrants. Within each arc line segment is a second arc line segment that is also colored. In the preferred embodiment, features are extracted from the combination of arc line segments: the location of the feature in the model is determined from the center of the circle shape. In this pattern, uniqueness is provided by the combinations of colors in the circle shapes. 811 shows an enlarged view of part of the pattern: 813 indicates an instance of an element of the pattern: the arrow of 813 points to the center of a circle shape.

The pattern of 820 is composed of elements that are non-overlapping cross shapes. The arm of each cross is a colored line segment. Next to each arm is an additional line segment, which is also colored. In the preferred embodiment, features are extracted from the combination of line segments: the location of the feature in the model is determined from the center of the cross shape. In this pattern, uniqueness is provided by the combinations of colors in the line segments. 821 shows an enlarged view of part of the pattern: 823 indicates an instance an element of the pattern: the arrow of 823 points to an intersection at the center of a cross shape.

The pattern of 830 is composed of elements that are non-overlapping diamond shapes. Each edge of the diamond shape is a colored line segment. Within the outermost edges of each diamond shape is a second set of edges composed of line segments that are also colored. In the preferred embodiment, features are extracted from the combination of line segments: the location of the feature in the model is determined from the center of the diamond shape. In this pattern, uniqueness is provided by the combinations of colors in the diamond shapes. 831 shows an enlarged view of part of the pattern: 833 indicates an instance of an element of the pattern: the arrow of 833 points to the center of a diamond shape.

Aids to the Making of Images

A number of optional aids may be employed in using the garment.

Reference Object

For some applications, it may be difficult to determine the correct dimensional scale for the model from the images used in making the model. A reference object that has a known dimension may be included in one or more of the images with the pattern, as an aid in addressing this problem. The reference object may be combined with another object.

Figure 9:
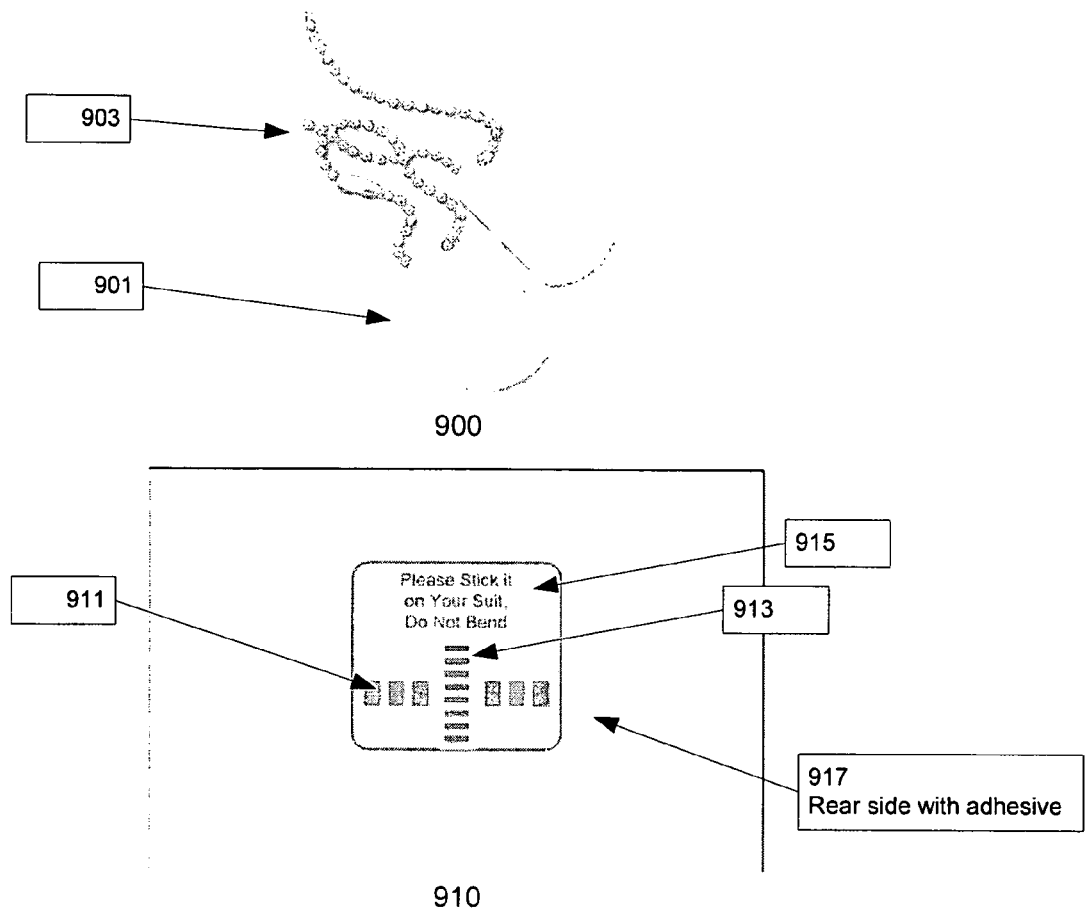
FIG. 9 shows examples of reference objects of the preferred embodiment.

Examples of preferred embodiments of an optional reference object are shown in FIG. 9.

910 shows an example of a preferred embodiment of a reference object, consisting of a rectilinear tag that attaches to the garment: alternatively the tag may be permanently part of the garment. The front side of the tag is printed with instructions at 915

"Please stick it on your suit. Do not bend."

The back side of the tag at 917 has an adhesive surface for holding the tag on the garment during use. Also printed on the tag is a set of reference marks 911, 913 of fixed dimensions and known spacing between the marks, thus each providing a reference for dimensional scale. The marks are colored so that they may be more readily detected in an image. The tag may also be of known dimensions, and may also be used as a reference for dimensional scale.

A further example of an optional reference object of the preferred embodiment is shown at 900. 900 shows two instances of a reference object consisting of a tag like a military identification tag such as 901. The tag is of known dimensions, thus providing a reference for dimensional scale. The tag may be worn conveniently around the neck suspended by chain 903.

The optional reference object need not be provided with the garment. An object available to the individual may be used as a reference object. For example, a standard sheet of letter paper of A4 size or 8½"×11" size has a number of known dimensions, and may thus provide a reference for dimensional scale. The sheet of paper can be positioned so that it is visible in a number of the images with the garment.

Posing Guide

In systems employing structure-from-motion techniques such as the preferred embodiment, models are produced from information obtained from images made from different camera positions with respect to the surface. It may be a problem for the individual to know which camera positions are to be preferred.

Figure 10:
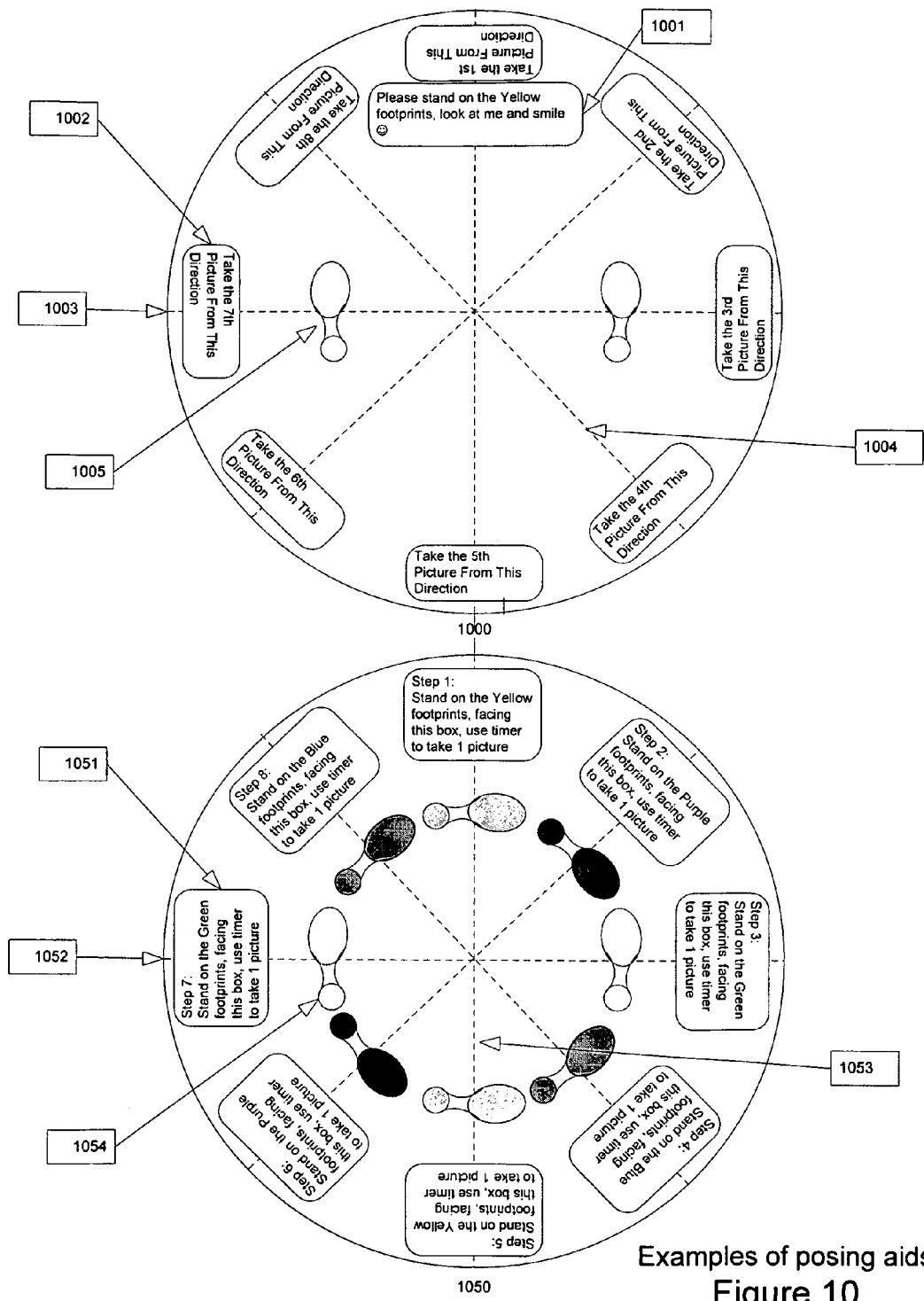
FIG. 10 shows examples of posing aids.

An aid that may be used to address problems of this kind is a posing guide that aids the person wearing the garment in producing a set of images that are good for producing the model. A posing guide may be static, or may be interactive. One example of a preferred embodiment for a static posing guide is a printed mat, shown in FIG. 10. The printed mat contains printed instructions and symbols showing how and where the individual should pose for the different images. Instructions may of course be iconic or textual.

1000 shows one example of a printed mat. The example of 1000 is intended for a use in which the individual stands in approximately the same position, and a person assisting the individual makes images with a camera from different directions: the posing guide shows favored locations for the camera when making images. 1001 advises the individual first to stand on the Yellow Footprints 1005. The mat has printed instructions for each image in turn, such as the one at 1002

"Take the $7^{th}$ picture from this direction".

Reference lines such as 1003 and 1004 show the directions for the images.

1050 shows a second similar example of a printed mat. The example of 1050 is intended for a use in which the camera is left in a fixed position and the individual poses in different positions relative to the camera for each image. The mat has several colored "foot" icons showing where to stand or move, such as at 1054. 1052 and 1053 are two of several reference lines showing direction. The mat has printed instructions, such as the one at 1051

"Step 7: Stand on the green footprints".

An icon of known dimension on the printed mats may be used as optional reference object if a number of the images show both the icon and the garment in the same image. Of course, any embodiment of a posing guide may be employed, as may other embodiments of other aids.

Physical Aid

Some techniques of structure-from-motion may produce better results when the parts of the surface have the same or nearly the same relative position in a number of images. An aid in dealing with this problem is a physical aid to the individual which helps the individual pose in the same fashion in each image. For example, a physical aid may be used that provides a stable resting support for the individual's hands, to make it more comfortable to hold the arms in the same pose.

FIG. 7 shows an illustration of a preferred embodiment of a physical aid at 716. The physical aid is a stand for supporting the arms while posing. The physical aid may also be combined with another object, such as a reference object aid: this is illustrated at 708. The physical aid may also simply be a suitable object available to the individual. For example, a high-backed chair may be suitable for the user to rest hands on the top of the chair.

Forms of Aids

Aids may be provided in various forms, and may be provided in any combined form, such as printed information for a posing guide on a physical aid.

Providing Images for Analysis

The images may be provided to the modeling system for computing the three-dimensional model by any convenient means or form. For example, images may be provided electronically or as photographs, or film media or video recording or video files. Images in electronic form may be convenient for providing to a personal computer, or to the Internet, depending on the implementation of a particular embodiment. As a further example, if a web-cam camera is used, the pictures may be provided to the system automatically. For an embodiment in which the personal computer contains software for performing one or more steps of producing the model from the images, intermediate results such as improved-quality images or features or feature correlations or the model itself may be uploaded to a server for further processing including application processing.

Exemplary Preferred Embodiment Employing a Web-Cam Camera

A web-cam or other video camera may be used to make the images for producing the model. The video camera may make images continuously. The individual may make multiple views at different angles for the point of the view conveniently by moving in front of the camera.

Figure 11:
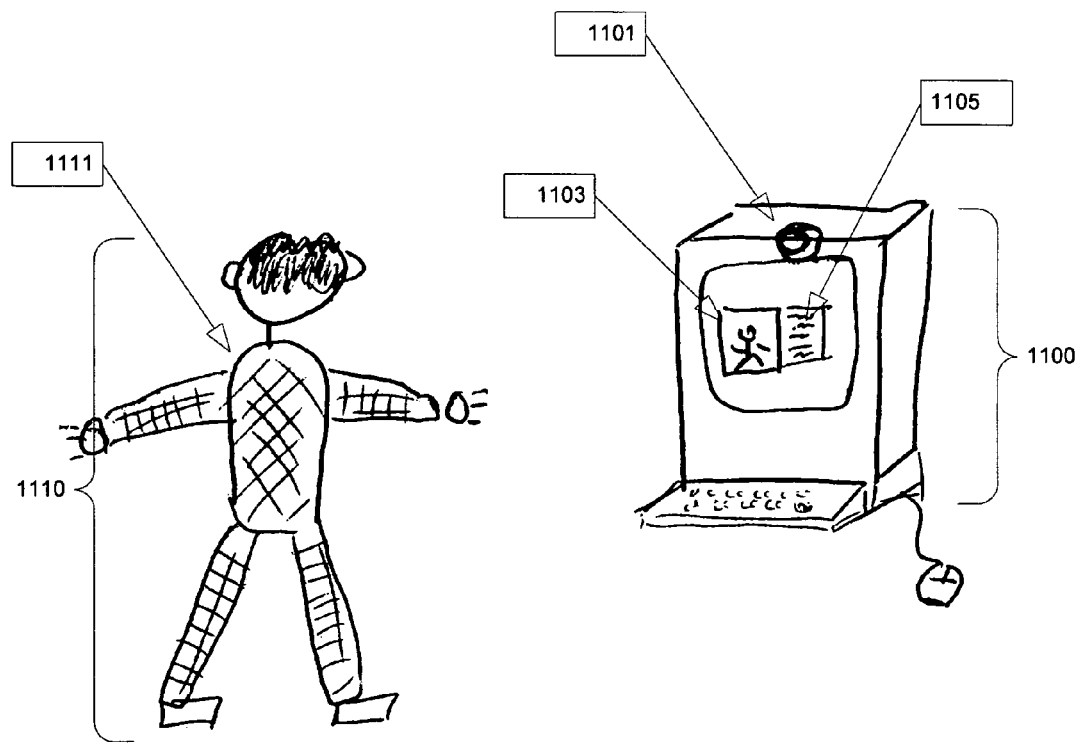
FIG. 11 illustrates a preferred embodiment using a webcam camera.

FIG. 11 illustrates a preferred embodiment incorporating a web-cam camera. A personal computer 1100 available to the individual 1110 wearing the garment 1111 executes software to display instructions on how to pose or how to move for the images: display in this context includes any form of output to the individual, for example it may be in the form of audible output. A web-cam camera 1101 of the personal computer is controlled by the software to make the images. The software may display the live image 1103 captured by the camera in the computer's display, so that the individual can see readily whether an appropriate image will be made, and to adjust the pose, the lighting, the distance the individual is from the camera, or other aspects for the image. The software may display a posing guide in the form of instructions shown at 1105. The software may also display each image after it is made, if the images are made as static images rather than a video, so that the individual can reject images that do not appear satisfactory.

The computer may also be programmed with algorithms to verify the quality of the images and provide the user with real-time feedback advice at 1105. For example, the software may determine whether a sufficient number of pattern elements are visible in the image, whether enough of the individual's body is visible, or whether a sufficient number of features can be extracted from the image, or where the lighting is proper for good results.

In this example embodiment of a web-cam camera or other embodiments, the computer may also execute software to construct a three-dimensional model, and show a graphical representation to the individual of the model. The computer may also show the individual a virtual image of something that may be produced using the model, such as clothes made according to the shape of the model, displayed on the actual shape of the individual's body.

Using Three-dimensional Models Produced Using the Garment

Modeling Objects from which it May be Difficult to Make Measurements

In addition to the uses previously mentioned, the garment may be employed in the making of models for objects for which it may be difficult to make measurements. For example, children or animals that are not adequately cooperative as subjects to be measured by traditional means, may be measured by dressing the subject in a form of the garment, and creating a model of the shape. The garment is particularly suitable for motion capture, as the garment when worn stays with the body of the subject whose motion is being captured.

Uses of Models of Parts of the Human Body

Fitting of Clothes

The model may be used as a specification for producing clothing that will fit the individual for whose body shape the model was made.

The model may be used to determine a selection of ready-made or pre-sized clothing that will fit the individual.

The garment may be part of a kit for making models for constructing clothes that fit: the kit may consist of the garment and access to instructions on its use. Depending on the needs of the particular application, the kit may include further items, such as a printed mat as described above, a reference object, a web-cam camera and software as described above. Another form of the kit may consist of a garment and a stand for holding a cell-phone with built-in camera: images may be submitted via E-mail directly from the cell-phone. In addition to the examples described above, the garment may be provided as part of a kit for a particular application. The kit may also include aids for using the garment, and the kit may include items for a particular application. For example, a kit may be provided for participating in computer games, or for medical or physical diagnosis or treatment, or for physical training. The garment may be a covering provided in a kit for making models of objects in situ.

Showing Changes in Body Shape

The model may be used to record the individual's body shape as a matter of record keeping, as in circumstances where the individual's body shape may change. For example, it may be used to record the individual's body shape before, during, and after changes occurring in a weight-loss program, as a result of bodybuilding, during pregnancy, during natural growth, body-altering surgery, or any other process resulting in a change in body shape.

The model can of course also be manipulated. Such manipulated models may be used to construct a representation of how the shape of part of an individual's body appears before a change, and how the body will appear after a change, for example a change from a weight-loss program, body-building, or a surgical procedure.

Anatomical and Physiological Applications

A model may be employed in physiological applications, such as surgical planning. A patient-specific three-dimensional body model can be combined with other input modalities such as Computer Tomography (CT), Magnetic Resonance Imaging (MRI) etc. to provide a comprehensive and anatomically accurate virtual representation of a patient for the purposes of surgical planning. Doctors may perform what-if scenario analysis or simulate the steps involved in a complicated operation by manipulating the model.

Avatars

The model may be used to produce an avatar for an individual or a virtual image of the individual's body shape. An avatar in this context is a digital representation of a person or entity.

The model may be used to produce a personalized electronic catalog for an individual with the individual's own body image or avatar, such as to show clothing or other articles, as they would actually appear when worn or used by that individual. The individual can use this to decide whether or not to chose or purchase the clothing, or to modify the fit of the clothing so that the clothing fits differently.

Other uses of avatars produced using the model include entertainment games that display images based on actual persons, such as sports-simulation games. The avatars may thus be images of specific sports individuals such that the images have the realistic and dynamic appearance of the actual individuals.

Statistics

A number of such models may be used as part of a data base by designers of clothing or objects that must fit human bodies or vice versa, as a statistical tool to understand body shape distribution in designing standard sizes for clothing or the objects.

Training and Education

Models, including dynamic models may be used to train people in fashion modeling, dance, or physical poise, by displaying realistic images of a user's actual appearance or how their appearance or posture may be changed.

The models may be used in virtual training systems, such as combat, emergency service, and sports training, to produce more realistic virtual images of a user, of virtual physical events and interactions with a virtual environment, or other users interacting in the virtual environment.

Motion Capture and Motion Input

Dynamic models produced using the garment may be used in motion capture, or as an input signal for computerized games, providing greater or more realistic control in the game. One advantage over techniques of prior art for motion capture, in addition to others such as those already mentioned, is that the pattern permits the use of structure-from-motion techniques to produce dynamic models of three-dimensional surfaces, rather than the locations of particular points such as the joints in the human body.

An avatar in a game may be controlled by the input signals to produce an avatar image that both follows a user's actual movements realistically, and further shows an avatar that closely resembles aspects of the user's actual physical appearance even as it changes.

Social Networking and Personal Choice

A model may be employed in social networking. For example, a user in a social networking community may provide an accurate three-dimensional model of her or his body as part of a profile in the social network community. The user or other users may then suggest products such as articles of clothing, or services such as activities: the articles of clothing can be displayed in a representation as they would actually appear if the user were wearing them, or the activities can be shown in a representation including the virtual appearance of the user. A user may then decide to purchase the articles or engage in the activity. The purchase may be made on-line in conjunction with the social networking system.

The model may be used to let the individual try on and select clothing, such as clothing the individual already possesses in a wardrobe or may purchase, in a virtual fashion. The model may be used to display virtual images of how combinations of articles of clothing will appear when the user is wearing them, or may suggest clothing by displaying it, so that the user can pick the combination they like for particular occasion or otherwise.

Within a Business Relationship

The garment may be obtained from an entity that is engaged in a business relationship with an individual. For example, the garment may be provided by an entity that offers to provide clothing to fit, or to provide assistance in the selection of clothing, as part of a business relationship.

The garment may be provided by an entity as part of a marketing or advertising effort. For example, the garment may be provided to encourage individuals to engage in an activity or business relationship in which the garment may be used for other purposes. Further, the pattern may be composed of elements that include logos, trademarks, or other business symbols.

Multi-Party Business Relationships

The garment may be provided to consumers by an entity to create models for use in a relationship with another entity. For example, an entity may provide a kit containing the garment and a number of aids for making images for producing models. The models produced may be stored by the entity, such as on a web server. The consumer may then order clothing from a second entity's web site, and the clothing may be fitted according to models of the consumer stored by the first entity. Fitting may occur either by providing the model to the second entity or having the second entity provide a description of the clothes to be fitted to the first entity. Further, the second entity may provide a link to the first entity's web server for the convenience of the consumer in providing access to or creating the model. Similarly, the first entity may provide links to second entities that make use of the models provided by the first entity.

Conclusion

The foregoing Detailed description has disclosed to those skilled in the relevant technologies how to use the inventors' techniques for providing correlatable features as required to achieve a particular accuracy in modeling surfaces and has disclosed the best mode presently known to the inventors of implementing those techniques. As will be immediately apparent to those skilled in the relevant technologies, the patterns of the techniques may be applied in ways other than those disclosed herein to the surfaces being modeled and any kind of pattern may be used whose elements permit features to be extracted with sufficient density for the degree of accuracy required for the model and also provide the extracted features with the degree of uniqueness needed for correlation.

While the lack of any requirement for precision in making the images makes the techniques particularly useful in situations where the images from which the models are made are provided by consumers, the techniques are useful in any model making situation where a high density of correlatable features are required. Moreover, it will also be apparent to those skilled in the relevant technologies that the correlated features produced using the techniques may be advantageously employed with any kind of feature-based modeling technique. For all of the foregoing reasons, the Detailed Description is to be regarded as being in all respects exemplary and not restrictive, and the breadth of the invention disclosed herein is to be determined not from the Detailed Description, but rather from the claims as interpreted with the full breadth permitted by the patent laws.

The invention claimed is:

1. A method of obtaining a set of images from which a three-dimensional model of a surface may be made, the method comprising the steps of:
    applying a covering having a pattern to the surface to be modeled, the pattern of the covering as applied to the surface including locally non-repetitive pattern elements that have a uniqueness within the surface; and
    making the set of images of the surface after the covering has been applied, the pattern elements being perceptible in the images, features needed to make the model being extractable from the perceptible pattern elements, and the uniqueness of the perceptible pattern elements being used to correlate the extracted features.

2. The method set forth in claim 1 wherein:
    the three-dimensional model is required to have a particular accuracy; and
    the pattern's elements have a density in the pattern such that the features that are extractable from the perceptible pattern elements have a density in the model which is sufficient give the three-dimensional model the particular accuracy.

3. The method set forth in claim 2 wherein:
    the three-dimensional model includes submodels that are required to have different particular accuracies; and
    the pattern is applied to the surface such that the densities of the pattern's elements in the areas of the object corresponding to the submodels are sufficient to give the extracted features the particular accuracies in the submodels, wherein feature density in the pattern elements is higher in at least one of (a) areas corresponding with submodels where higher accuracy is needed than in areas corresponding with submodels where lower accuracy is needed and (b) areas corresponding with submodels having greater local curvature than in areas corresponding with submodels having lesser local curvature.

4. The method set forth in claim 1 wherein:
    the image is made using a camera; and
    in the step of making a set of images, information concerning the camera's position relative to the surface when the image was made need not be associated with the image.

5. The method set forth in claim 4 wherein:
    the images are made using an indication of favored camera locations for making the images.

6. The method set forth in claim 1 further comprising the step of:
    providing a reference object for use in the step of making the images, the reference object appearing in an image of the set and indicating a scale of the model.

7. The method set forth in claim 1 wherein:
    in the step of making the set of images, the surface to be modeled is in motion as the set of images is made; and
    the three-dimensional model of the surface is a dynamic model.

8. The method set forth in claim 1 wherein:
    the covering with the pattern is applied to the surface by conforming the covering with the pattern to the surface.

9. The method set forth in claim 1 wherein:
    the surface to be modeled is a portion of a living entity's body; and
    the covering is a garment worn by the entity, the garment covering the portion of the body whose surface is to be modeled.

10. The method set forth in claim 9 further comprising the steps of:
    receiving the garment; and
    providing the set of images to a model making entity.

11. The method set forth in claim 10 wherein:
    the step of making the set of images is performed using a camera to which a processor has access;
    the processor and the model making entity have access to a network; and
    the processor performs the step of providing the set of images to the model making entity via the network.

12. A method of making a three-dimensional model of a surface from a set of images of the surface, the images in the set having been made of the surface after application of a covering having a pattern to the surface, the pattern as applied including locally non-repetitive pattern elements that have a uniqueness within the surface and the pattern elements being perceptible in the images of the set, the method comprising the steps of:
    extracting the features needed to make the model from the perceptible pattern elements;
    using the uniqueness of the perceptible pattern elements to correlate the extracted features; and
    using the correlated extracted features to make the three-dimensional model.

13. The method set forth in claim 12 further comprising the step of:
    making a use of the three-dimensional model.

14. The method set forth in claim 12 further comprising the step of:
 providing the 3-dimensional model to a model using entity for a use.

15. The method set forth in claim 12 further comprising the steps of:
 receiving information from a model using entity for a use; and
 performing the use for the model using entity.

16. The method set forth in claim 12 wherein:
 the use of the three-dimensional model is making a copy of the surface.

17. The method set forth in claim 12 wherein:
 the use of the three-dimensional model of the surface is fitting an item to the surface.

18. The method set forth in claim 12 wherein:
 the surface of which the model is to be made is a portion of a living entity's body;
 the covering is in the form of a garment; and
 the pattern is applied to the surface by covering the portion with the garment that has the pattern and is worn by the entity.

19. The method set forth in claim 18 wherein:
 the use of the three-dimensional model is fitting an item of clothing to the entity.

20. The method set forth in claim 18 wherein:
 the use of the three-dimensional model is constructing an avatar of the entity.

21. The method set forth in claim 20 wherein:
 the avatar represents the entity in a virtual world.

22. The method set forth in claim 20 wherein:
 the avatar is used to display an item of merchandise for the avatar's entity.

23. A storage medium which is accessible to a processor, the storage medium being characterized in that:
 the storage medium includes code which, when executed by the processor, performs the method set forth claim 12.

24. A covering for use in making a three-dimensional model of a surface from images of the surface as covered by the covering,
 the covering being characterized in that:
 the covering is conformable to the surface to be modeled;
 the covering has a pattern which includes locally non-repetitive pattern elements having a uniqueness within the surface as covered, the pattern elements being perceptible in the images, features needed to make the model being extractable from the perceptible pattern elements. and the uniqueness of the perceptible pattern elements being used to correlate the extracted features.

25. The covering set forth in claim 24 wherein:
 the surface of which the model is to be made is a portion of a living entity's body; and
 the covering is a garment worn by the entity, the garment covering the portion of the body whose surface is to be modeled.

26. A kit for use in making a set of images from which a three-dimensional model of a surface may be made, the kit comprising:
 a covering that is conformable to the surface to be modeled and that has a pattern which includes pattern elements having a uniqueness within the surface as covered by the covering, the pattern elements being perceptible in the images, features needed to make the model being extractable from the perceptible pattern elements, and the uniqueness of the perceptible pattern elements being used to correlate the extracted features; and
 at least one aid to making the set of images.

27. The kit set forth in claim 26 wherein:
 the images are made without precise calibration of camera location; and
 the aid is an indication of favored camera locations for making the images.

28. The kit set forth in claim 26 wherein:
 the aid is a reference object for use in making the images, the reference object appearing in an image of the set and indicating a scale of the model.

29. The kit set forth in claim 28 wherein:
 the reference object is a component of the covering.

30. The method of claim 12 further comprising the step of providing the covering having the pattern to a user for applying to the surface to be modeled.

31. The method of claim 1, wherein the uniqueness of the pattern elements includes unique color combinations in the pattern elements.

* * * * *